(12) United States Patent
Gadient et al.

(10) Patent No.: US 9,693,938 B2
(45) Date of Patent: Jul. 4, 2017

(54) POWDEROUS FORMULATIONS OF ORGANIC ACIDS OR ESTERS HAVING AN AROMATIC RING SYSTEM

(71) Applicant: DSM IP ASSETS B.V., Heerlen (NL)

(72) Inventors: Martin Gadient, Kaiseraugst (CH); Marie Agnes Aeschlimann, Kaiseraugst (CH); Romeo Isner, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/907,656

(22) PCT Filed: Jul. 25, 2014

(86) PCT No.: PCT/EP2014/066050
§ 371 (c)(1),
(2) Date: Jan. 26, 2016

(87) PCT Pub. No.: WO2015/011271
PCT Pub. Date: Jan. 29, 2015

(65) Prior Publication Data
US 2016/0166483 A1    Jun. 16, 2016

(30) Foreign Application Priority Data

Jul. 26, 2013 (EP) .................................... 13178144

(51) Int. Cl.
| | | |
|---|---|---|
| *A23L 33/15* | (2016.01) | |
| *A23L 3/3508* | (2006.01) | |
| *A61K 47/02* | (2006.01) | |
| *A61K 8/24* | (2006.01) | |
| *A61K 8/36* | (2006.01) | |
| *A61K 9/14* | (2006.01) | |
| *A61Q 19/00* | (2006.01) | |
| *A61K 8/25* | (2006.01) | |
| *A61K 8/02* | (2006.01) | |
| *A61K 8/368* | (2006.01) | |
| *A23P 10/40* | (2016.01) | |

(52) U.S. Cl.
CPC .............. *A61K 8/25* (2013.01); *A23L 3/3508* (2013.01); *A23L 33/15* (2016.08); *A23P 10/40* (2016.08); *A61K 8/0241* (2013.01); *A61K 8/24* (2013.01); *A61K 8/36* (2013.01); *A61K 8/368* (2013.01); *A61Q 19/00* (2013.01); *A23V 2002/00* (2013.01); *A61K 9/14* (2013.01); *A61K 47/02* (2013.01); *A61K 2800/52* (2013.01)

(58) Field of Classification Search
CPC ........ A23L 33/15; A23L 3/3508; A23P 10/40; A23V 2002/00; A61K 2800/52; A61K 47/02; A61K 8/0241; A61K 8/24; A61K 8/25; A61K 8/36; A61K 8/368; A61K 9/14; A61Q 19/00
See application file for complete search history.

(56) References Cited

U.S. PATENT DOCUMENTS

| | | |
|---|---|---|
| 5,008,118 A | 4/1991 | Iwanami et al. |
| 5,100,592 A | 3/1992 | Sparks et al. |
| 2005/0191393 A1* | 9/2005 | Postma ................... A23B 7/10 426/324 |

FOREIGN PATENT DOCUMENTS

| | | |
|---|---|---|
| EP | 0 611 590 | 8/1994 |
| FR | 2 797 452 | 2/2001 |
| GB | 2 042 866 | 10/1980 |
| GB | 2 252 710 | 8/1992 |
| JP | S64-83044 | 3/1989 |
| WO | WO 2006/038134 | 4/2006 |
| WO | WO 2009/024475 | 2/2009 |
| WO | 2012/089729 | 7/2012 |

OTHER PUBLICATIONS

Pohanish et al. (Wiley Guide to Chemical Incompatibilities 2009. John Wiley & Sons. p. 122).*
Niacin Safety Data Sheet (2012; 10 pages).*
Nagy (Development and Control of Dust Explosions 1983; CRC Press ; 12 pages).*
Barton (Dust Explosion Prevention and Protection 2002 IChemE; 2 pages).*
Class Names and the International Numbering System for Food Additives 2002 [online] retrieved from: ftp://ftp.fao.org/codex/Meetings/CCFAC/ccfac31/INS_e.pdf on Oct. 13, 2016; 34 pages).*
International Search Report for PCT/EP2014/066050 dated Oct. 22, 2014, six pages.
Written Opinion of the ISA for PCT/EP2014/066050 dated Oct. 22, 2014, six pages.
Ducatillon et al., Sugar dust and prevention of explosions. (translated), *Sucrerie Francaise* 1984, vol. 125, No. 82, 1984, four pages.
Kordylewski et al., "Comparison of NaHCO3 and NH4H2P04 effectiveness as dust explosion suppressants", *Combustion and Flame*, vol. 90, No. 4, Sep. 1, 1992, pp. 344-345.
Amyotte et al., "Solid inertants and their use in dust explosion prevention and mitigation", *Journal of Loss Prevention in the Process Industries*, vol. 19, No. 2-3, Mar. 1, 2006, pp. 161-173.
Krasnyansky et al., "Prevention and suppression of explosions in gas-air and dust-air mixtures using powder aerosol-inhibitor", *Journal of Loss Prevention in the Process Industries*, vol. 19, No. 6, Nov. 1, 2006, pp. 729-735.
The First Office Action, CN Appln. No. 201480041773.2, Nov. 2, 2016.

* cited by examiner

*Primary Examiner* — Ernst V Arnold
(74) *Attorney, Agent, or Firm* — Nixon & Vanderhye P.C.

(57) ABSTRACT

The present invention relates to improved powderous formulations comprising a high amount of at least one organic acids or esters having an aromatic ring system, as well as to the production of such formulations.

9 Claims, No Drawings

POWDEROUS FORMULATIONS OF ORGANIC ACIDS OR ESTERS HAVING AN AROMATIC RING SYSTEM

This application is the U.S. national phase of International Application No. PCT/EP2014/066050 filed 25 Jul. 2014 which designated the U.S. and claims priority to EP Patent Application No. 13178144.5 filed 26 Jul. 2013, the entire contents of each of which are hereby incorporated by reference.

The present invention relates to improved powderous formulations as well as to the production of such formulations.

Powderous formulations of organic acids or esters having an aromatic ring system are very common and useful formulations.

Examples of such organic acids or esters are niacin and benzoic acid.

Niacin (also known as vitamin B3, nicotinic acid and vitamin PP) is an essential human nutrient.

A lack of niacin in the diet can cause the disease pellagra, which is characterized by diarrhea, dermatitis, and dementia, as well as "necklace" lesions on the lower neck, hyperpigmentation, thickening of the skin, inflammation of the mouth and tongue, digestive disturbances, amnesia, delirium, and eventually death, if left untreated. A lack of niacin can also cause psychiatric symptoms such as irritability, poor concentration, anxiety, fatigue, restlessness, apathy, and depression.

Benzoic acid and its salts are used as food preservative.

When these organic acids are used in powder form, these formulations do unfortunately have a tendency to explode.

Even when the powder has a prominent amount of larger particles, there is always a certain amount of small particles present. These small particles are responsible for the explosion risk.

Dust explosions are a huge risk in any processes wherein powders are used. Therefore there is a need for powderous formulations with low explosion hazard. But nevertheless the powderous formulations must still have the essential (and advantageous) features of a powder, such as free flowable, easy to transport, easy to dosage etc.

It is known from the prior art that certain auxiliary compounds and carrier material, can minimize the explosion risk of powderous formulation comprising vitamin E.

Due to the importance of such non-explosive formulations, there is always a need for improved formulation.

Surprisingly it was found that powderous formulations comprising a high amount (at least 65 weight-% (wt-%)) of at least one compound of formula (I)

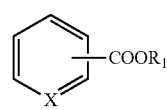

(I)

wherein
X is —N— or —CH— and
$R_1$ is H or a $C_1$-$C_4$ alkyl moiety, and comprising one or more specific compounds (auxiliary compound), and optionally at least one carrier material
do have a low risk of explosion.

Therefore the present application relates to powderous formulations (I) comprising (i) 65-95 weight-% (wt-%), based on the total weight of the powderous formulation, of at least one compound of formula (I)

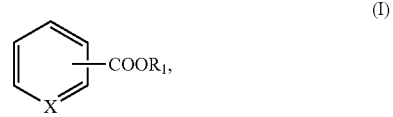

(I)

wherein
X is —N— or —CH— and
$R_1$ is H or a $C_1$-$C_4$ alkyl moiety, and
(ii) 5-35 wt-%, based on the total weight of the powderous formulation, of at least one auxiliary compound selected from the group consisting of aluminum ammonium sulphate, aluminum potassium sulfate, ammonium acetate, ammonium bisulphite, ammonium carbonate, ammonium chloride, ammonium dihydrogen phosphate, ammonium hydrogen carbonate, bentonite, montmorillonite, calcium aluminates, calcium carbonate, calcium silicate, synthetic calcium sulphate dihydrate, calcium sulfate, kaolinitic clays (such as Kaolin), diatomaceous earth, perlite, potassium bisulphite, potassium hydrogen carbonate, potassium sulphate, potassium carbonate, sepiolitic clays, silicic acid, synthetic sodium aluminosilicate, sodium aluminosulfate, sodium bisulphate, sodium carbonate, sodium chloride, sodium hydrogen carbonate, sodium sulphate, vermiculite, calcium carbonate, magnesium carbonate, calcareous marine algae, magnesium oxide, magnesium sulphate, dicalcium phosphate, tri-calcium phosphate, mono-dicalcium phosphate, defluorinated rock-phosphate, monocalcium phosphate, calcium-magnesium phosphate, mono-ammonium phosphate, magnesium phosphate, sodium-calcium-magnesium phosphate, mono-sodium phosphate, glycerol, propylene glycol (E 1520), glyceryl triacetate (E1518), sorbitol (E420), polydextrose, lactic acid and urea, and optionally
(iii) up to 40 wt-%, based on the total weight of the powderous formulation, of a carrier material.

It is clear that the sum of all the wt-%'s always add up to 100.

Preferably, $R_1$ in the definition of formula (I) is H, $CH_3$, $CH_2CH_3$, $(CH_2)_2CH_3$ and $(CH_2)_3CH_3$. More preferably $R_1$ is H or $CH_3$.

Therefore the present invention relates to a powderous formulation (I'), which is formulation (I) wherein $R_1$ in the definition of formula (I) is H, $CH_3$, $CH_2CH_3$, $(CH_2)_2CH_3$ and $(CH_2)_3CH_3$.

Therefore the present invention relates to a powderous formulation (I"), which is formulation (I) wherein $R_1$ in the definition of formula (I) is H or $CH_3$.

In the context of the present invention the specific compounds (ii) are also defined as auxiliary compounds.

Compounds of formula (Ia) and (Ib)

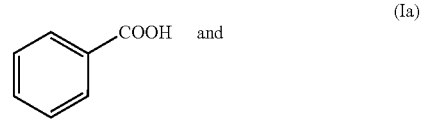

(Ia)

and

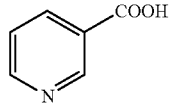

are preferred.

Therefore the present invention relates to a powderous formulation (II), which is formulation (I), (I') or (I"), wherein the compound of formula (I) is a compound of formula (Ia) and/or (Ib)

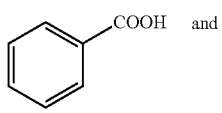

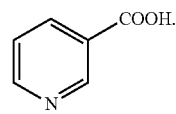

Preferably, the auxiliary compounds have an average particle size (d 0.5) (in the powder formulation) of 10 μm-100 μm.

Therefore the present invention relates to a powderous formulation (III), which is formulation (I), (I'), (I") or (II), wherein the auxiliary compounds have an average particle size (d 0.5) (in the powder formulation) of 10 μm-100 μm.

Furthermore a preferred embodiment of the present invention relates to a powderous formulation comprising 70-90 wt-%, based on the total weight of the powderous formulation, of at least one compound of formula (I).

Furthermore a preferred embodiment of the present invention relates to a powderous formulation comprising 10-30 wt-%, based on the total weight of the powderous formulation, of at least one auxiliary compound.

Therefore the present invention also relates to a formulation (IV), which is formulation (I), (I'), (I"), (II) or (III), wherein the formulation comprises 70-90 wt-%, based on the total weight of the powderous formulation, of at least one compound of formula (I).

Therefore the present invention also relates to a formulation (V), which is formulation (I), (I'), (I"), (II), (III) or (IV), wherein the formulation comprises 10-30 wt-%, based on the total weight of the powderous formulation, of at least one auxiliary compound.

The average particle sizes are measured by a Malvern Master Sizer 2000. During this laser diffraction measurement, particles are passed through a focused laser beam. These particles scatter light at an angle that is inversely proportional to their size. The angular intensity of the scattered light is then measured by a series of photosensitive detectors. The map of scattering intensity versus angle is the primary source of information used to calculate the particle size. For the measurement of dry materials such as the applied additives, a dry powder feeder (Malvern Scirocco) was used.

The explosion hazard of powders (dusts) is usually measured by a standardized method (EN 13821:2002 (Determination of minimum ignition energy of dust/air mixtures)). This is the method which is used for the determination of all MIE values in this patent application. This method allows to determining the minimum ignition energy (MIE) of a powder. The MIE is the minimum amount of energy required to ignite a combustible vapor, gas or dust cloud, for example due to an electrostatic discharge. MIE is measured in joules (J).

The average size of the powder particles for the measurement according to the procedure in EN 13821:2002 is ≤63 μm.

All the MIE values in this patent application are determined by using a modified Hartmann tube (type MIKE 3) available from Adolf Kühner AG (Birsfelden, CH). This equipment is specially designed to allow the measurement of very low ignition energies. This is achieved by having different capacitors installed. The capacitors are designed to store the energy of 1 mJ, 3 mJ, 10 mJ, 30 mJ, 100 mJ, 300 mJ and 1000 mJ.

When measuring the MIE of commercially available powderous formulations comprising at least one compound of formula (I), they are usually in the range of 1-3 mJ. This means that a very low amount of energy is sufficient to initiate an explosion.

On the other hand, the formulations according to the present invention have MIE values in the range of 10-1000 mJ (or even more than 1000 mJ).

Therefore the present invention relates to formulations (VI), which are formulations (I), (I'), (I"), (II), (III), (IV) or (V), with MIE values of 10-1000 mJ (determined by the method of EN 13821:2002). It can be even higher than 1000 mJ.

The formulations according to the present invention are dry powders. But depending on the process of production as well as the storage conditions, the formulations can comprise some water. The water content is usually below 5 wt-%, based on the total weight of the formulation.

Therefore a further embodiment of the present invention relates to formulations (VII), which are formulations (I), (I'), (I"), (II), (III), (IV), (V) or (VI), wherein 0-5 wt-%, based on the total weight of the formulation, of water is present.

Preferably the powderous formulations do not comprise other ingredients/compounds than as disclosed above. They do not contain any commonly used stabilisers, surface active ingredients or sugars.

The compounds of formula (I) can be from a natural source or they can be synthesised. Due to the nature of either the isolation process or the process of production, it is possible that traces of side products are present.

The carrier material optionally used in the formulations according to the present invention are commonly known and used carrier material. A suitable carrier material is synthetically produced precipitated silica or formiate (such as calcium formiate). This carrier material consists of porous particles. Other suitable carrier materials are proteins, starches, lignosulfonates and gums.

Preferred formulations of the present invention are formulations (VIII), wherein formulations (I), (I'), (I"), (II), (III), (IV), (V), (VI) or (VII) comprise
(ii) 5-35 wt-% (preferably 10-30 wt-%), based on the total weight of the formulation, of at least one compound selected from the group consisting of ammonium dihydrogen phosphate, (purified) diatomaceous earth, potassium hydrogen carbonate, potassium sulphate, potassium carbonate, sodium chloride and sodium hydrogen carbonate.

More preferred are formulations (VIII'), which are formulations (VIII) with MIE values of 10-1000 mJ (determined by the method of EN 13821:2002). It can be even higher than 1000 mJ.

Furthermore preferred are formulations (VIII"), which are formulations (VIII') wherein the auxiliary compound has an average particle size (d 0.5) of 10 μm-100 μm.

Also preferred are formulations (IX), which are formulations (I), (I'), (I"), (II), (III), (IV), (V), (VI), (VII), (VIII), (VIII') or (VIII"), which comprise
(iii) up to 40 wt-%, based on the total weight of the formulation, of at least one carrier material chosen from the group consisting of synthetically produced precipitated silica, formate (such as calcium formate), proteins, starches, lignosulfonates and gums.

An especially preferred embodiment of the present invention relates to formulations (X), consisting of
(i) 65-95 wt-% (preferably 70-90 wt-%), based on the total weight of the powderous formulation, of

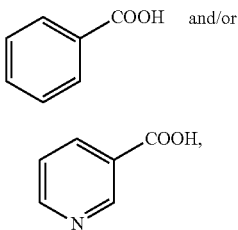

and
(ii) 5-35 wt-% (preferably 10-30 wt-%), based on the total weight of the powderous formulation, of at least one auxiliary compound selected from the group consisting of ammonium dihydrogen phosphate, (purified) diatomaceous earth, potassium hydrogen carbonate, potassium sulphate, potassium carbonate, sodium chloride, sodium sulphate and sodium hydrogen carbonate, and
0-5 wt-%, based on the total weight of the powderous formulation, of water.

To produce a powder according to the present invention (formulations (I), (I'), (I"), (II), (III), (IV), (V), (VI), (VII), (VIII), (VIII'), (VIII"), (IX) or (X)) the at least one compound of formula (I) is blended with at least one auxiliary compound. This process can be carried out by using any usually used blenders. The sequence of adding the compounds is not essential for the invention.

In case a carrier material is used the powder according to the present invention (formulations (I), (I'), (I"), (II), (III), (IV), (V), (VI), (VII), (VIII), (VIII'), (VIII"), (IX) or (X)) is produced by spraying the least one compound of formula (I) onto the carrier material and then at least one auxiliary compound is added and the formulation is blended.

It is also possible that at least one compound of formula (I) is sprayed onto a mixture of at least one carrier material and at least one auxiliary compound.

All the above disclosed formulations (I), (I'), (I"), (II), (III), (IV), (V), (VI), (VII), (VIII), (VIII'), (VIII"), (IX) or (X) can be used as such or in food products, feed products and personal care products.

All the above disclosed formulations (I), (I'), (I"), (II), (III), (IV), (V), (VI), (VII), (VIII), (VIII'), (VIII"), (IX) or (X) can be used as such in the production of food products, feed products and personal care products.

Furthermore the invention also relates to food products, feed products and personal care products comprising at least one formulations (I), (I'), (I"), (II), (III), (IV), (V), (VI), (VII), (VIII), (VIII'), (VIII"), (IX) or (X).

The invention is illustrated by the following Examples. All temperatures are given in ° C. and all parts and percentages are related to the weight.

EXAMPLES

Example 1

900 g benzoic acid (purity 99.9%) was filled into an appropriate blender (Nauta) and 63 g sodium chloride having a particle size, analysed by laser diffraction, of 54 μm were added. Then 27 g silicon dioxide and 5 g calcium formiate and 5 g mono calcium phosphate were added and the mixture was blended for 10 minutes. The obtained free flowing white powder was filled into a container.

The blend was then air classified in an appropriate apparatus (Alpine Multiprocess unit 100 AFG/50ATP), using an air flow of 60 m³/h and rotation speed of the sifter wheel of 2200 rpm, and the fines collected.

Assessed by laser diffraction, the particles averaged 34 μm, sodium chloride content was 20.2 wt-% and benzoic acid content was 70.1 wt-%. The fines were analyzed according to the above mentioned EN 13821:2002 and minimum ignition energy was found to be 10-30 mJ.

Example 2

750 g nicotinic acid (Rovimix® Niacin from DSM) (purity 99.5%) was filled into an appropriate blender (Turbula) and 250 g sodium chloride having a particle size, analysed by laser diffraction, of 54 μm was added, the mix then blended for 10 minutes. The material was then transferred to a Retsch Grindomixer and milled (10,000 rpm/1 min.). The median size of this material was 23 μm. The obtained white powder was filled into a container.

The powder was analysed according to the above mentioned EN 13821:2002 and the minimum ignition energy was found to be 300-1000 mJ.

The invention claimed is:
1. A powderous formulation comprising
(i) 70-95 wt %, based on the total weight of the powderous formulation, of at least one compound of formula (I):

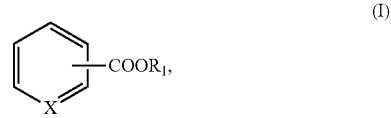

wherein
X is —N— or —CH—, and
$R_1$ is H or a $C_1$-$C_4$ alkyl moiety, and
(ii) 10-30 wt %, based on the total weight of the powderous formulation, of at least one auxiliary compound selected from the group consisting of ammonium dihydrogen phosphate, purified diatomaceous earth, potassium hydrogen carbonate, potassium sulphate, potassium carbonate, sodium chloride and sodium hydrogen carbonate, wherein
the powderous formulation has minimum ignition energy (MIE) value of 10 mJ or greater.
2. The powderous formulation according to claim 1, wherein the at least one compound of formula (I) is at least one compound of formula (Ia) and (Ib):

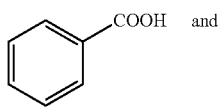

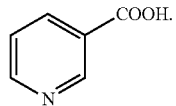

3. The powderous formulation according to claim 1, wherein the auxiliary compounds have an average particle size (d 0.5) in the powder formulation of 10 μm-100 μm.

4. The powderous formulation according to claim 1, wherein the compounds of formula (I) is present in an amount sufficient to impart a MIE value to the formulation of 10-1000 mJ.

5. The powderous formulation according to claim 1, wherein the compounds of formula (I) is present in an amount sufficient to impart a MIE value to the formulation of more than 1000 mJ.

6. The powderous formulation according to claim 1, comprising 0-5 wt-%, based on the total weight of the formulation, of water.

7. A powderous formulation according to claim 1, wherein the formulation further comprises:
   (iii) up to 40 wt-%, based on the total weight of the formulation, of at least one carrier material selected from the group consisting of synthetically produced precipitated silicas, formiates, proteins, starches, lignosulfonates and gums.

8. A powderous formulation consisting of:
   (i) 70-90 wt-%, based on the total weight of the powderous formulation, of at least one compound of formula (Ia) and (Ib):

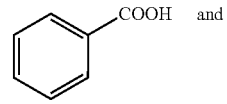

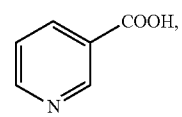

and
   (ii) 10-30 wt-%, based on the total weight of the powderous formulation, of at least one auxiliary compound selected from the group consisting of ammonium dihydrogen phosphate, diatomaceous earth, potassium hydrogen carbonate, potassium sulphate, potassium carbonate, sodium chloride, sodium sulphate and sodium hydrogen carbonate, and
   (iii) 0-5 wt-%, based on the total weight of the powderous formulation, of water, wherein
   the powderous formulation has a minimum ignition energy (MIE) value of 10 mJ or greater.

9. A food product, feed product or personal care product comprising the powderous formulation according to claim 1.

* * * * *